United States Patent [19]

Grinberg

[11] Patent Number: 5,759,185
[45] Date of Patent: Jun. 2, 1998

[54] SURGICAL INSTRUMENT

[75] Inventor: Alexander Grinberg, Newton, Mass.

[73] Assignee: Smith & Nephew, Inc., Memphis, Tenn.

[21] Appl. No.: 727,169

[22] Filed: Sep. 30, 1996

Related U.S. Application Data

[63] Continuation of Ser. No. 328,450, Oct. 24, 1994, abandoned.

[51] Int. Cl.$^6$ .................... A61B 17/00; A61B 17/14
[52] U.S. Cl. ............................ 606/80; 606/180
[58] Field of Search ........................... 606/53, 79, 80, 606/1, 167, 171, 169, 159, 180, 170; 128/749–154; 604/902

[56] References Cited

U.S. PATENT DOCUMENTS

| | | | |
|---|---|---|---|
| 3,584,629 | 6/1971 | Hoef et al. | 606/180 |
| 4,203,444 | 5/1980 | Bonnell et al. | |
| 4,274,414 | 6/1981 | Johnson et al. | |
| 4,646,738 | 3/1987 | Trott | 606/180 |
| 4,834,729 | 5/1989 | Sjostrom | |
| 4,842,578 | 6/1989 | Johnson et al. | |
| 4,983,179 | 1/1991 | Sjostrom | |
| 5,228,459 | 7/1993 | Caspari et al. | 606/80 |
| 5,269,785 | 12/1993 | Bonutti et al. | 606/80 |
| 5,320,635 | 6/1994 | Smith | 606/167 |
| 5,322,505 | 6/1994 | Krause et al. | |
| 5,366,468 | 11/1994 | Fucci et al. | |

OTHER PUBLICATIONS

Smith & Nephew Endoscopy Inc. TurboCutter Instrument (Part No. 3449).

Aesculap®, Aesculap® Arthroscopy System, product literature, including GB 616 Reamer (p. 13).

*Primary Examiner*—Glenn K. Dawson
*Attorney, Agent, or Firm*—Fish & Richardson P.C.

[57] ABSTRACT

The surgical tool of a surgical instrument is configured to have a plurality of tissue-cutting edges circumferentially spaced by flutes disposed in an exterior surface of the tool. Each flute includes an aperture that intersects an interior chamber of the tool for conveying tissue fragments cut by the edges into the chamber. The chamber communicates with an interior passage of a rotating tube on which the tool is mounted. During operation, the tissue fragments (e.g., bone fragments) cut by the rotating surgical tool are conveyed into the flutes and through the apertures into the chamber for removal from the surgical site through the interior passage of the tube, while the instrument remains in situ for further cutting.

19 Claims, 3 Drawing Sheets

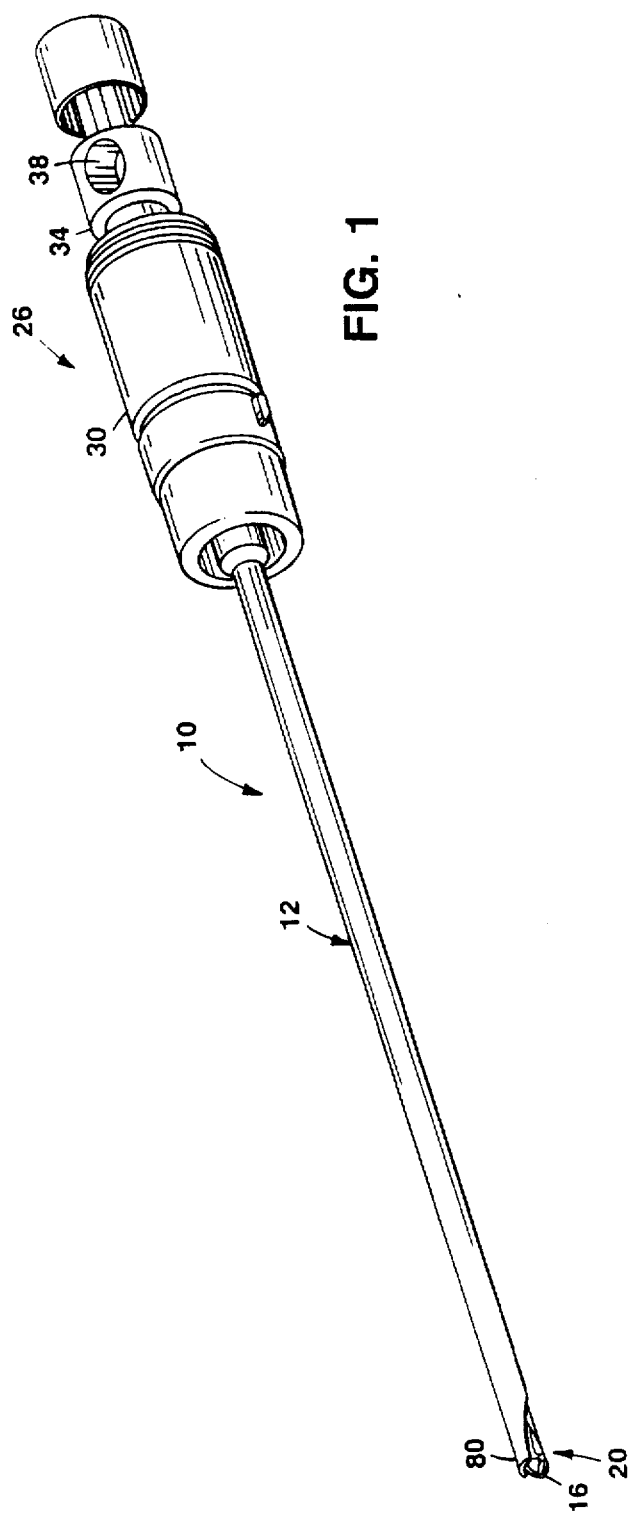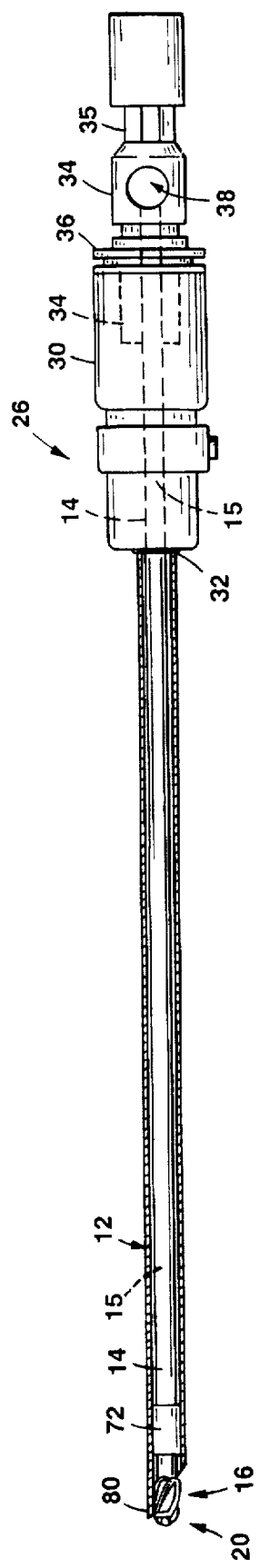

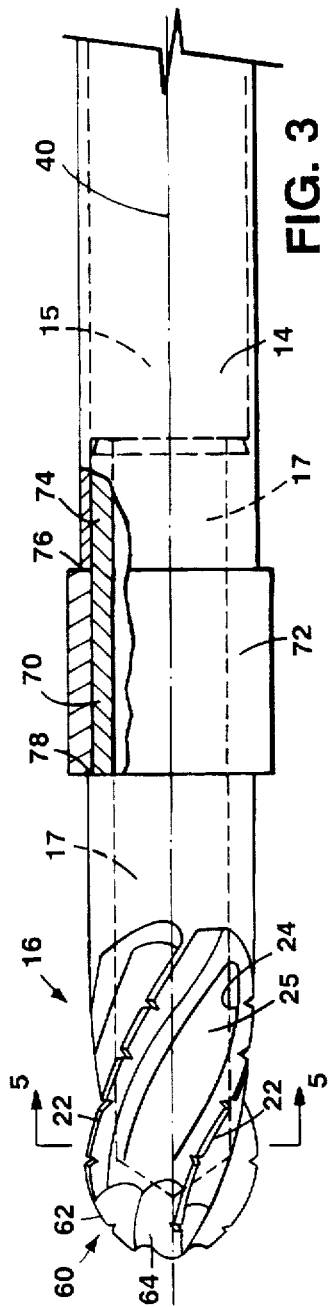
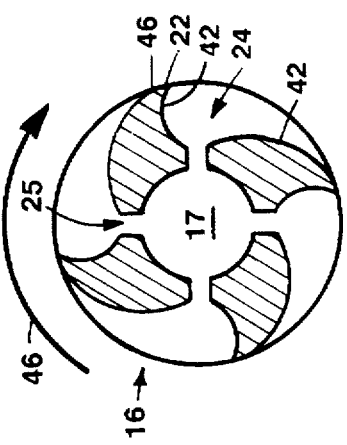
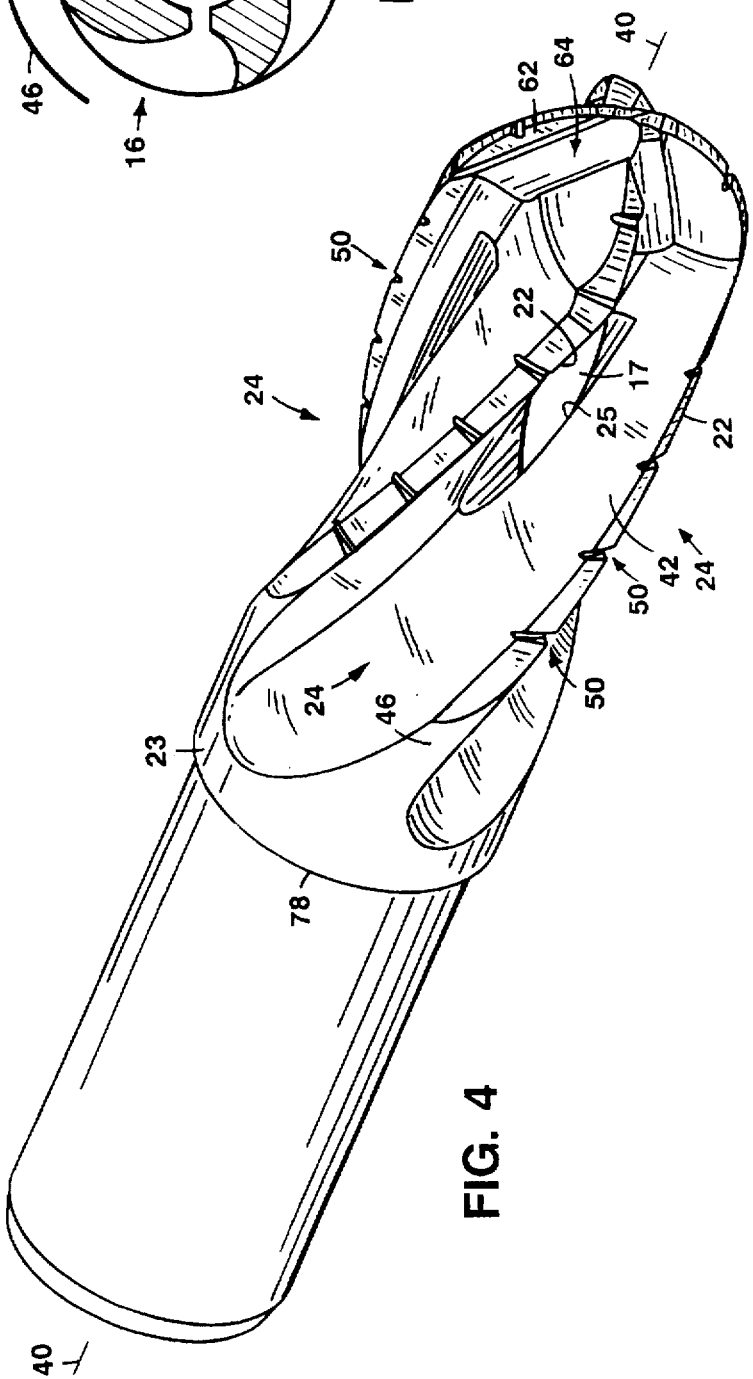

SURGICAL INSTRUMENT

This is a continuation of application Ser. No. 08/328,450 filed Oct. 24, 1994, now abandoned.

BACKGROUND OF THE INVENTION

This invention relates to arthroscopic surgical instruments, and in particular to powered arthroscopic surgical instruments.

Powered arthroscopic surgical instruments typically include a stationary outer tube within which an inner tube that carries a surgical tool on its distal end is rotated by a motor. Body tissue exposed to the surgical tool through an opening in the outer tube is cut by the rotating tool. Tissue fragments cut by the tool and irrigating fluid from the surgical site are drawn through a suction passage defined by the interior of the inner tube in response to a vacuum applied at the proximal end of the instrument. Examples of such surgical instruments are described in U.S. Pat. Nos. 4,203,444, 4,274,414, 4,834,729, 4,842,578, 4,983,179, and 5,322,505, all of which are assigned to the assignee of the present invention and incorporated herein by reference.

The configuration of the surgical tool is a function of the type of body tissue that the instrument is designed to cut. For example, in a so-called "abrader" for sculpting bone tissue, the surgical tool is a solid, fluted burr mounted on the distal end of the inner tube. The burr (which is, e.g., spherical or oval in shape) usually includes a series of axially elongated, helical cutting edges spaced circumferentially around the burr by the flutes. The inner tube typically includes a hole spaced proximally of the burr through which bone fragments cut by the rotating burr are conveyed into the interior of the tube by the applied suction.

Because of the high rotational speeds typically encountered (e.g., up to 5000 rpm) in powered arthroscopic surgical instruments, the interface between the inner and outer tubes should minimize the friction between them. In some instruments, this is done by making the inner tube from soft stainless steel and coating the interior of the outer tube with a relatively soft, lubricating metal (such as silver). The low friction avoids "shedding" of the tube materials and lessens the risk of the inner tube seizing within the outer tube.

SUMMARY OF THE INVENTION

This invention features configuring the surgical tool of a surgical instrument to have a plurality of tissue-cutting edges circumferentially spaced by flutes disposed in an exterior surface of the tool, with each of the flutes including an aperture that intersects an interior chamber of the tool for conveying tissue fragments cut by the edges into the chamber for suction removal.

One general aspect of the invention is the surgical tool itself. Another general aspect of the invention is a surgical instrument in which an inner tube that carries the surgical tool on its distal end rotates within an outer member. The interior chamber of the tool communicates with an interior passage in the inner tube. The tissue fragments cut by the rotating surgical tool and conveyed into the chamber are transported by the applied suction through the inner tube to the proximal end of the instrument, where the fragments are removed via a vacuum fitting, while the instrument remains in situ for further cutting.

The invention eliminates the need for the tissue fragments to travel longitudinally along the exterior of the surgical tool and the inner tube before entering the suction passage. As a result, the risk of the surgical instrument becoming clogged with the tissue fragments is reduced. Further, arranging the apertures circumferentially around the tool (rather than providing a single opening in the inner tube proximally of the tool, as in prior schemes) helps maintain the inner tube balanced during operation. This reduces vibration, even at high speeds of rotation. In addition, the apertures can be made relatively large in size, thereby allowing even large fragments to be drawn into the chamber without clogging. The apertures are easily accessible for cleaning after use without first disassembling the surgical instrument.

Preferred embodiments include the following features.

The flutes are helical and are elongated along a longitudinal axis of the surgical tool. The cutting edges are generally oriented at a helix angle (e.g., between 20° and 30°) relative to the longitudinal axis. Each flute includes an exterior surface of the surgical tool, recessed from the cutting edges, in which the aperture is formed.

The surgical instrument is a so-called "abrader," and thus the cutting edges are constructed and arranged to cut bone tissue. At least one (and preferably all) of the cutting edges includes one or more notches therein. The notches enable the cutting edges to grind the bone into smaller fragments, thereby enhancing abrading and suction removal efficiency.

In one embodiment, the cutting edges extend to the distal tip of the tool to enable end-on cutting. The distal extensions of the cutting edges are oriented transversely to the longitudinal axis and extend radially from the center of the distal tip of the tool.

The surgical tool is exposed to the tissue through an opening in a distal region of the outer member. The surgical tool and inner tube are radially spaced from the outer member to reduce friction during rotation. The inner tube rotates within a bushing radially disposed between the inner tube and the outer member proximate to the surgical tool serves. The bushing serves as a bearing to help prevent the rotating surgical tool from contacting the outer member when side-loads are imposed on the tool (e.g., when abrading bone). The inner tube may be fixed to the bushing, or not.

The proximal region of the outer member is mounted to a housing, which rotatably receives a base to which the proximal region of the inner tube is secured. The base is equipped with the vacuum fitting.

Another aspect of the invention features a method of performing surgery using the surgical instrument described herein.

Other features and advantages of the invention will become apparent from the following description, and from the claims.

BRIEF DESCRIPTION OF THE DRAWINGS

FIG. 1 is a perspective view of a surgical instrument.

FIG. 2 is a side view, partially cut away, of the surgical instrument, showing an inner tube within an outer tube.

FIG. 3 is a side view, partially cut away, of a surgical tool mounted on the distal end of the inner tube.

FIG. 4 is a perspective view of the surgical tool.

FIG. 5 is a cross-sectional view of the surgical tool, taken along line 5—5 of FIG. 3.

DESCRIPTION OF PREFERRED EMBODIMENTS

Figure 6:
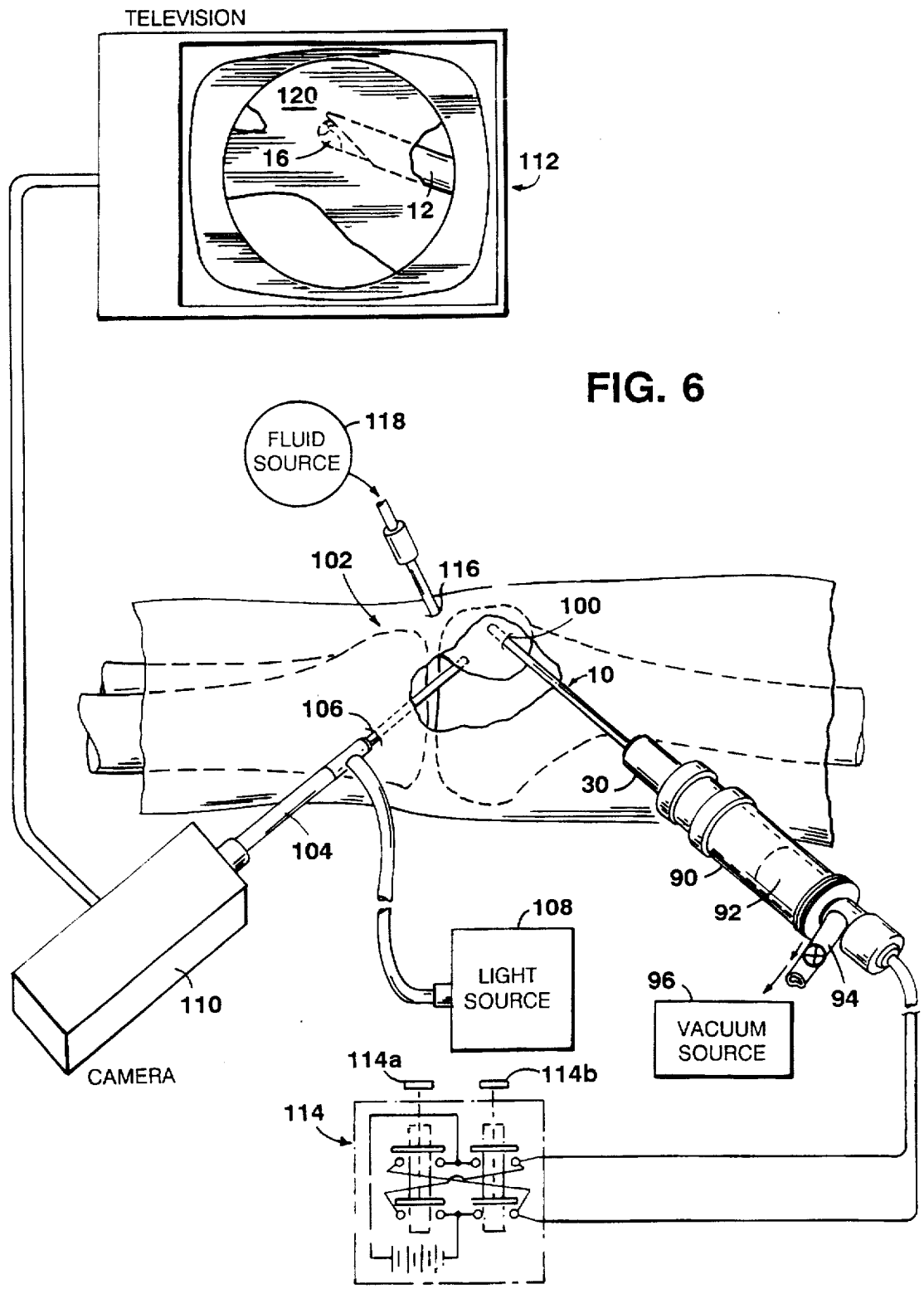
FIG. 6 shows the surgical instrument in use.

Referring to FIGS. 1–3, surgical instrument 10 includes a stationary outer tube 12 within which a inner tube 14 is rotatably disposed. An abrading surgical tool 16 mounted to a distal end of inner tube 14 cuts bone tissue exposed to tool 16 through an opening 20 in the distal end of outer tube 12. Surgical tool 16 includes four sharpened cutting edges 22 circumferentially spaced from each other by elongated, helical flutes 24 disposed in an exterior surface 23 of surgical tool 16. Flutes 24 each include an aperture 25 that intersects an interior chamber 17 of surgical tool 16.

Inner tube 14 includes a suction passage 15 that communicates with chamber 17. During use, as inner tube 14 rotates, bone tissue exposed to surgical tool 16 is cut by rotating cutting edges 22, and the resulting bone fragments are immediately driven by the rotation of inner tube 14 into flutes 24 and through apertures 25 into chamber 17. Suction applied to passage 15 at the proximal end 26 of instrument 10 transports the bone fragments proximally through inner tube 14 for removal from the body, while surgical instrument 10 remains in situ for further cutting.

The proximal end of outer tube 12 is rigidly mounted to a housing 30 at proximal end 26. Housing 30 rotatably receives a base 34 to which the proximal end of inner tube 14 is attached. Base 34 is retained in housing 30 by a pliable fitting 36. Passage 15 terminates proximally in a suction port 38 in base 34. This construction is described, for example, in the above-discussed U.S. Pat. No. 5,322,505.

During use, proximal end 26 of instrument 10 is inserted into a handpiece 90 (shown in FIG. 6), which includes a motor for engaging the proximal end 35 of base 34, which serves as a drive shaft for inner tube 14. Operation of the motor rotates inner tube 14 (and thus surgical tool 16) within outer tube 12. (One example of such a handpiece is described in U.S. Pat. No. 4,705,038, assigned to the assignee of the present invention, and incorporated by reference herein.) Fitting 36 provides a fluid-tight seal with handpiece 90. As discussed below, handpiece 90 applies suction from an external vacuum source 96 to suction port 38 to enable the bone fragments and irrigating fluid from the surgical site to be withdrawn from inner tube 14.

Surgical instrument 10 is preferably disposable, that is, the device is made to be discarded after a single (or relatively few) uses. Outer and inner tubes 12, 14 are made from stainless steel (such as 304 SST). Housing 30 and base 34 are plastic. Of course, other materials may be used instead if, e.g., surgical instrument 10 is to be autoclavable and reusable.

Surgical tool 16 is shown in detail in FIG. 4. Surgical tool 16 is a so-called "abrader" or "burr". That is, cutting edges 22 are constructed and arranged to cut relatively hard tissue, such as bone. Surgical tool 16 is made from 440A stainless steel (SST) and is hardened to a 50–55 Rockwell hardness. Cutting edges 22 are defined by a set of axially elongated, helical flutes 24 formed (such as by machining) in exterior surface 23 of surgical tool 16. As a result, cutting edges 22 are helical in shape and are axially elongated generally along the longitudinal axis 40 of surgical tool 16. Cutting edges 22 are distributed around the periphery 46 of surgical tool 16 and are equally circumferentially spaced from each other by flutes 24. It thus will be appreciated that surgical tool 16 resembles an augured drilling implement.

Unlike a typical drilling implement, however, surgical tool 16 is hollow, being equipped with the aforementioned chamber 17 (which serves as a distal extension of inner tube passage 15). Apertures 25, which extend along the majority of the length of flutes 24, intersect chamber 17 for conveying the tissue fragments severed by cutting edges 22 into chamber 17, and thence into tube passage 15. Apertures 25 are equally spaced around the circumference of surgical tool 16, due to the uniform spacing of flutes 24. Like flutes 24, apertures 25 are axially elongated. The elongation of apertures 25 allows even relatively large tissue fragments to pass through them without clogging.

As shown in FIG. 4, each flute 24 defines an exterior surface 42 of surgical tool 16 that is recessed from exterior surface 23 at the periphery 46 of the tool. Each aperture 25 is formed in a surface 42 at the bottom of the recess. The length and width dimensions of apertures 25 are a function of the diameter of chamber 17 and the depth of flutes 24, and should be made sufficiently large to provide an efficient suction path between flutes 24 and chamber 17. The diameter of chamber 17 is constant along its length.

Cutting edges 22 are oriented so that the majority of their lengths lie at a helix angle of between 20° and 30° with respect to longitudinal axis 40. An angle of 20° is preferred. The relatively small inclination of cutting edges 22 (and thus of flutes 24) reduces the tendency of surgical tool 16 to propel irrigating fluid proximally as inner tube 14 rotates, and thus enhances suction into chamber 17 through apertures 25.

A set of V-shaped, circumferentially aligned notches 50 (each of which defines an angle in the "V" of about 60°) are disposed in cutting edges 22. Notches 50 are relatively small, for example, extending only a few thousandths of an inch into cutting edges 22, but they serve to interrupt each cutting edge, dividing it into a series of shorter segments. The shorter segments produce correspondingly smaller bone fragments during abrading. This further reduces the risk of clogging apertures 25, chamber 17, or passage 15.

The distal tip 60 of surgical tool 16 is generally spherical and is provided with a set of distal extensions 62 of cutting edges 22 for end-on cutting. Distal cutting edge extensions 62 are oriented transversely to longitudinal axis 40 and extend radially from the center of distal tip 60 to periphery 46 of surgical tool 16, where they meet the remainder of cutting edges 22. Grooves 64 channel bone fragments cut by edges 62 into flutes 24 for suction removal via apertures 25, chamber 17, and passage 15.

Surgical tool 16 is manufactured from a cylindrical, stainless steel blank with a spherical tip as follows. First, a reduced-diameter shank 70 (FIG. 3) is machined at the proximal end of the blank, and chamber 17 is drilled out. Then, the blank is heat treated to harden it to the required Rockwell hardness. Flutes 24 are then machined to define helical cutting edges 22 and form apertures 25. As discussed, the depth of flutes 24 and the diameter of chamber 17 define the size of apertures 25. Distal tip 60 is gashed to create transverse cutting edges 62. Finally, notches 50 are formed using a cylindrical grinding wheel.

Referring again to FIG. 3, during assembly of instrument 10, a phosphor-bronze bushing 72 is inserted over reduced-diameter shank 70 of surgical tool 16. The proximal end 74 of shank 70 is then secured within the distal end of inner tube 14 by any suitable technique (such as spot, laser or electron beam welding, brazing, swaging, or gluing). Bushing 72 is captured between the distal tip 76 of inner tube 14 and shoulder 78 between shank 70 and the remainder of tool 16, and surgical tool 16 is free to rotate within bushing 72.

Inner tube 14, surgical tool 16, and bushing 72 are inserted as a unit through housing 30 into outer tube 12 until base 34 becomes seated within housing 30. The outer diameter of inner tube 14 is significantly less than the inner diameter of outer tube 12 to provide clearance between tubes 12, 14. The outer diameter of bushing 72 is, however, only slightly smaller than the inner diameter of outer tube 12 to provide a tight fit therebetween. Bushing 72 thus serves as a bearing for surgical tool 16 against side-loads imposed during abrading.

The distal end of outer tube 12 may be of any suitable configuration. In the embodiment shown, tube 12 includes a distal sheath 80 (FIG. 1) that defines a side-facing and open-ended opening 20 and partially shields surgical tool 16 from adjacent tissue. An example of this configuration is shown in the aforementioned U.S. Pat. No. 4,842,578. Alternatively, the distal end of outer tube 12 can be completely open.

Referring to FIG. 6, in use, surgical instrument 10 is inserted into the distal end of handpiece 90. As discussed above, handpiece 90 includes a motor 92 for engaging proximal end 35 of base 34 to rotate inner tube 14. Handpiece 90 also includes a vacuum fitting 94 through which suction from a vacuum source 96 is applied to suction port 38 (FIG. 2) of instrument 10.

The distal end of surgical instrument 10 is introduced through a puncture wound 100 into a patient's knee joint 102, below the patella. An endoscope 104 inserted into joint 102 through a second puncture 106 both provides illumination (from light source 108) to the surgical site and conveys an image of the surgical site to a television camera 110. The image is delivered by camera 110 to a television screen 112 for viewing by the surgeon. Alternatively, the surgeon may view the image using an eyepiece on endoscope 104, or the image may be recorded.

Joint 102 is inflated with fluid introduced through a third puncture wound 116 from a fluid source 118. The fluid irrigates the surgical site and provides a medium by which bone fragments cut by surgical tool 16 are drawn into chamber 17 (and thence into tube passage 15) by the suction applied by vacuum source 96.

The surgeon maneuvers the distal end of instrument 10 to urge surgical tool 16 (exposed by opening 20) against the tissue 120 (e.g., a section of bone) to be cut. The surgeon then activates motor 92 to rotate inner tube 14 and surgical tool 16. Motor 92 receives operating potential and current from power supply 114. The surgeon controls the rotational speed and direction (either unidirectional or oscillatory, although an abrader such as surgical tool 16 is typically operated in one direction only) using foot switches 114a, 114b, which control the magnitude and polarity of operating potential and current supplied by power supply 114 to motor 92. Motor 92 is capable of rotating inner tube 14 over a wide range of speeds, e.g., between 100 rpm and 5000 rpm, and can deliver a torque of up to 25 oz inches.

Cutting edges 22 of surgical tool 16 abrade bone tissue 120 as tool rotates. The aggressiveness of the abrading action is a function of the speed of rotation and the pressure applied to bone tissue 120 by the surgeon. The surgeon progressively abrades bone tissue 120 by moving instrument 10 from side to side and axially, while viewing the surgical site on television screen 112.

Bone fragments cut by edges 22 immediately enter flutes 24, due both to the rotation of surgical tool 16 and the suction applied by vacuum source 96. The applied suction also draws the fragments and the irrigation fluid through all apertures 25 into chamber 17, and thence into inner tube passage 15. The bone fragments and irrigation fluid are transported proximally through inner tube 14, and exit surgical instrument 10 at suction port 38.

Because apertures 25 are located between cutting edges 22—rather than spaced proximally from tool 16 on inner tube 14 (as in conventional instruments)—the fragments need not travel longitudinally along the exterior of surgical tool 16 and inner tube 14 before entering the suction passage. As a result, the risk that instrument 10 will become clogged by the tissue fragments is reduced. The notched configuration of cutting edges 22 helps ensure that the bone fragments are relatively small, further reducing chances of clogging.

The uniform spacing of apertures 25 around the periphery of tool 16 helps ensure that surgical tool 16 will remain in balance during rotation (e.g., because metal is removed uniformly around the circumference of tool 16 to form apertures 25, rather than in just one location, as in prior instruments). This helps reduce vibration of the rotating surgical tool 16, even at high speeds.

Bushing 72 serves as a bearing to maintain the rotating inner tube 14 and surgical tool 16 spaced from the inner surface of outer tube 12. Because bushing 72 is located immediately proximally of cutting surfaces 22, bushing 72 provides proximal support for surgical tool 16 against even relatively large side loads imposed when the surgeon urges tool 16 against bone tissue 120. This helps prevent tool 16 from contacting the inner surface of outer tube 12, thereby reducing wear of surgical tool 16 and avoiding "shedding" of steel fragments. The excellent bearing characteristics of the phosphor-bronze material of bushing 72 also contributes to reduced shedding. Moreover, bushing 72 helps reduce the risk of seizing (even at the high rotational speeds, e.g., 5000 rpm, at which abraders are typically operated) without need to coat the interior surface of outer tube 12 with a soft, precious metal (such as silver).

After use, surgical instrument 10 is cleaned if it is to be reused. The placement of apertures 25 between cutting edges 22, rather than proximally behind tool 16, renders apertures 25 readily accessible for cleaning.

Other embodiments are within the following claims.

For example, more or fewer cutting edges 22 and flutes 24 may be provided, as desired. In general, the number of cutting edges 22 is a function of the diameter of tool 16 and the desired aggressiveness of the cutting action.

More or fewer notches 50 than are shown in FIG. 4 may be provided, as desired, according to surgical tool 16 diameter and aperture 25 size. Notches 50 need not be disposed in every cutting edge 22.

Surgical tool 16 can have other "burr" shapes, if desired. Examples include tapered, oval, and round burrs. Surgical tool 16 need not be an abrader. Other configurations (such as so-called "shavers," "resectors," "end-cutters," etc.) for cutting, e.g., soft tissue are possible.

The diameter of chamber 17 may alternatively conform to the exterior shape of surgical tool 16. For example, chamber 17 may be tapered so that its diameter increases in the direction of the suction path (i.e., from distal tip 60 to shank 70). This would cause the width of apertures 25 to increase in the direction of the suction path.

Other cutting edge configurations are possible, depending upon the surgical application. In particular, cutting edges 22 need not be helical or, if helical, may be define other helix angles with respect to longitudinal axis 40.

Distal tip 60 of surgical tool 16 may be configured in other ways. For example, tip 60 may be blunt so that no end-on abrading action takes place. Alternatively, tip 60 may be configured for even more aggressive end-on cutting. Also, tip 60 need not be spherical. Possible alternative shapes include square, conical, convex, and concave.

Bushing 72 may alternatively be fixed to inner tube 14. In this case, bushing 72 is secured to shank 70 by, e.g., press fitting, brazing, gluing or other methods.

Opening 20 on outer tube 12 may take a variety of other shapes, depending on the type of surgery for which instrument 10 is intended. For example, opening 20 may have sharpened edges that co-act with surgical tool 16 (the size of which is selected to provide a close running fit with the sharpened edges of opening 20) to provide a shearing cutting action (either from the side only, or from the distal end and side).

Still other embodiments are within the scope of the claims.

What is claimed is:

1. A surgical instrument comprising
    an outer tube having an opening in a distal region thereof,
    an inner tube disposed for rotation within said outer tube and having an interior passage between a distal region and a proximal region thereof,
    a bone-abrading burr disposed on said distal region of said inner tube and positioned in said outer tube opening, said bone-abrading burr having a plurality of cutting edges configured to cut bone tissue, said cutting edges extending axially between a proximal end and a distal end thereof and being circumferentially spaced by flutes disposed in an exterior surface of said bone-abrading burr,
    said bone-abrading burr having an interior chamber that communicates with said passage, each of said flutes including an aperture that intersects said chamber, each said aperture being positioned circumferentially between said cutting edges and axially elongated along a major portion of said cutting edges between ends respectively disposed adjacent to said proximal and distal ends of said cutting edges so as to be exposed to tissue by said outer tube opening during rotation of said inner tube.

2. The surgical instrument of claim 1 further comprising a fitting in a proximal region of said inner tube that communicates with said passage for receiving suction, whereby tissue fragments cut by said cutting edges are withdrawn through said inner tube via said apertures and said passage.

3. The surgical instrument of claim 1 wherein said cutting edges and said flutes are elongated generally along a longitudinal axis of said inner tube.

4. The surgical instrument of claim 3 wherein said cutting edges are helical in shape.

5. The surgical instrument of claim 4 wherein said cutting edges are oriented at a helix angle of between 20° and 30° relative to the longitudinal axis.

6. The surgical instrument of claim 3 wherein each one of said flutes includes an exterior surface of said bone-abrading burr that is recessed from a periphery of said bone-abrading burr.

7. The surgical instrument of claim 1 wherein said cutting edges are elongated generally along a longitudinal axis of said inner tube, said bone-abrading burr further comprising at least one cutting edge oriented transversely to said longitudinal axis and disposed at a distal tip of said bone-abrading burr.

8. The surgical instrument of claim 7 further comprising a plurality of said transversely oriented cutting edges at least some of which form extensions of said elongated cutting edges at said distal tip.

9. The surgical instrument of claim 8 wherein said transverse cutting edges extend radially from a center of said distal tip and meet said elongated cutting edges at a periphery of said bone-abrading burr.

10. The surgical instrument of claim 1 wherein at least one of said cutting edges includes at least one notch disposed therein.

11. The surgical instrument of claim 1 further comprising a bushing radially disposed between said inner tube and said outer tube proximate to said bone-abrading burr.

12. The surgical instrument of claim 11 wherein said bone-abrading burr is rotatably disposed within said bushing.

13. The surgical instrument of claim 11 wherein said bushing is secured to said inner tube.

14. The surgical instrument of claim 1 wherein each said aperture is further configured so that all of said aperture is positioned distally of said proximal end of said cutting edges.

15. A surgical instrument comprising
    an outer tube having an opening in a distal region thereof, said opening being elongated along said outer tube between a proximal end and a distal end,
    an inner tube disposed for rotation within said outer tube, said inner tube having an interior passage between a distal region and a proximal region thereof,
    a bone-abrading burr disposed on said distal region of said inner tube and positioned in said outer tube opening, said bone-abrading burr having a plurality of cutting edges configured to cut bone tissue and circumferentially spaced by flutes disposed in an exterior surface of said bone-abrading burr,
    said bone-abrading burr having an interior chamber that communicates with said passage, each of said flutes including an aperture that intersects said chamber, each said aperture being configured so that a portion of said aperture is positioned distally of said proximal end of said outer tube opening.

16. The surgical instrument of claim 15 further comprising a housing mounted to a proximal region of said outer tube, and a base mounted to said proximal region of said inner tube and rotatably received by said housing, said base including a fitting that communicates with said passage for receiving suction, whereby the tissue fragments cut by said cutting edges are withdrawn through said inner tube.

17. The surgical instrument of claim 15 wherein each said aperture is further configured so that all of said aperture is positioned distally of said proximal end of said outer tube opening.

18. A bone-abrading burr for a surgical instrument, comprising
    a hollow body having an interior chamber therein,
    a plurality of cutting edges configured to cut bone tissue, said cutting edges extending axially between a proximal end and a distal end thereof and being circumferentially spaced by axially extending flutes disposed in an exterior surface of said body,
    at least one of said flutes including an aperture that intersects said interior chamber, said aperture being positioned circumferentially between said cutting edges and axially elongated along a major portion of said cutting edges between ends respectively disposed adjacent to said proximal and distal ends of said cutting edges.

19. A method of performing surgery, comprising
    providing a surgical instrument that includes
        an outer tube having an opening in a distal region thereof, an inner tube disposed for rotation within said outer tube, said inner tube having an interior passage between a distal region and a proximal region thereof, and a bone-abrading burr disposed on said distal region of said inner tube in said opening of said outer tube, said bone-abrading burr having a plurality of cutting edges configured to cut bone tissue, said cutting edges extending axially between a proximal end and a distal end thereof and being circumferentially spaced by flutes disposed in an exterior surface of said bone-abrading burr, said bone-abrading burr surgical tool having an interior chamber that communicates with said passage, each of said flutes including an aperture that intersects said chamber, each said aperture being positioned circumferentially between said cutting edges and axially elongated along a major portion of said cutting edges between ends respectively disposed adjacent to said proximal and distal ends of said cutting edges so as to be exposed to tissue by said outer tube opening during rotation of said inner tube, inserting said surgical instrument into the body so that said bone-abrading burr is disposed adjacent to bone tissue to be cut, operating said surgical instrument to cause said inner tube to rotate within said outer tube so that said cutting edges cut said bone tissue and resulting bone tissue fragments are conveyed into said chamber through said aperture, and applying suction to a proximal region of said surgical instrument that communicates with said passage so that the bone tissue fragments cut by said cutting edges and conveyed into said chamber through said aperture are withdrawn through said inner tube via said passage.

* * * * *